(12) United States Patent
Lee et al.

(10) Patent No.: US 6,254,849 B1
(45) Date of Patent: Jul. 3, 2001

(54) ZEOLITE SSZ-52

(75) Inventors: Gregory S. Lee, San Ramon; Stacey I. Zones, San Francisco, both of CA (US)

(73) Assignee: Chevron U.S.A. Inc., San Francisco, CA (US)

( * ) Notice: Subject to any disclaimer, the term of this patent is extended or adjusted under 35 U.S.C. 154(b) by 0 days.

(21) Appl. No.: 09/363,076

(22) Filed: Jul. 28, 1999

(51) Int. Cl.⁷ .................................................. C01B 39/48
(52) U.S. Cl. ............................................ 423/706; 423/718
(58) Field of Search ...................... 423/706, 718

(56) References Cited

U.S. PATENT DOCUMENTS

| | | | |
|---|---|---|---|
| 3,054,657 | * 9/1962 | Breck | 423/718 |
| 4,562,166 | * 12/1985 | Valyocsik | 423/706 |
| 5,200,377 | 4/1993 | Zones et al. | 502/62 |
| 5,271,921 | 12/1993 | Nakagawa | 423/702 |
| 5,273,736 | 12/1993 | Nakagawa | 423/702 |

FOREIGN PATENT DOCUMENTS 0 092 946 * 11/1983 (EP).

* cited by examiner

*Primary Examiner*—David R. Sample
(74) *Attorney, Agent, or Firm*—Richard J. Sheridan

(57) ABSTRACT

The present invention relates to new crystalline zeolite SSZ-52 prepared using a quaternary ammonium cation templating agent having the structure

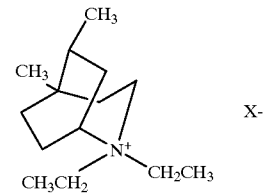

where X— is an anion which is not detrimental to the formation of the SSZ-52. SSZ-52 is useful in catalysts for hydrocarbon conversion reactions.

9 Claims, No Drawings

ZEOLITE SSZ-52

BACKGROUND OF THE INVENTION

1. Field of the Invention

The present invention relates to new crystalline zeolite SSZ-52, a method for preparing SSZ-52 using the quaternary ammonium cation templating agent N,N-diethyl-5,8-dimethyl-2-azonium bicyclo[3.2.2]nonane, and processes employing SSZ-52 as a catalyst.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

SUMMARY OF THE INVENTION

The present invention is directed to a family of crystalline molecular sieves with unique properties, referred to herein as "zeolite SSZ-52" or simply "SSZ-52". Preferably, SSZ-52 is obtained in its aluminosilicate form. As used herein, the term "aluminosilicate" refers to a zeolite containing both alumina and silica.

In accordance with this invention, there is provided a zeolite having a mole ratio of about 6–50 of an oxide selected from silicon oxide, germanium oxide and mixtures thereof to an oxide selected from aluminum oxide, gallium oxide, iron oxide, and mixtures thereof and having, after calcination, the X-ray diffraction lines of Table I below.

The present invention further provides such a zeolite having a composition, as synthesized and in the anhydrous state, in terms of mole ratios as follows:

| | |
|---|---|
| $YO_2/W_2O_3$ | 6–50 |
| $M_{2/n}/YO_2$ | 0.03–0.25 |
| $Q/YO_2$ | 0.02–0.08 | wherein Y is silicon, germanium or a mixture thereof; W is aluminum, gallium, iron, or mixtures thereof; M is an alkali metal cation, alkaline earth metal cation or mixtures thereof, n is the valence of M (i.e., 1 or 2); and Q is a quaternary ammonium cation having the structure

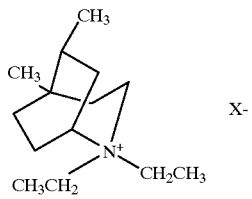

Template A

The zeolite has, after calcination, the X-ray diffraction lines of Table I below.

In accordance with this invention, there is also provided a zeolite prepared by thermally treating a zeolite having a mole ratio of an oxide selected from silicon oxide, germanium oxide and mixtures thereof to an oxide selected from aluminum oxide, gallium oxide, iron oxide, and mixtures thereof of about 6–50 at a temperature of from about 200° C. to about 800° C., the thus-prepared zeolite having the X-ray diffraction lines of Table I. The present invention also includes this thus-prepared zeolite which is predominantly in the hydrogen form, which hydrogen form is prepared by ion exchanging with an acid or with a solution of an ammonium salt followed by a second calcination.

Also provided in accordance with the present invention is a method of preparing a crystalline material comprising an oxide of a first tetravalent element and an oxide of a second tetravalent element which is different from said first tetravalent element, trivalent element, pentavalent element or mixture thereof, said method comprising contacting under crystallization conditions sources of said oxides and a templating agent comprising Template A.

The present invention additionally provides a process for converting hydrocarbons comprising contacting a hydrocarbonaceous feed at hydrocarbon converting conditions with a catalyst comprising the zeolite of this invention. The zeolite may be predominantly in the hydrogen form. It may also be substantially free of acidity.

Further provided by the present invention is a hydrocracking process comprising contacting a hydrocarbon feedstock under hydrocracking conditions with a catalyst comprising the zeolite of this invention, preferably predominantly in the hydrogen form.

This invention also includes a dewaxing process comprising contacting a hydrocarbon feedstock under dewaxing conditions with a catalyst comprising the zeolite of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the zeolite of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising at least one Group VIII metal and the zeolite of this invention. The zeolite may be predominantly in the hydrogen form.

In accordance with this invention, there is also provided a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and the zeolite of this invention, preferably predominantly in the hydrogen form. The catalyst may be a layered catalyst comprising a first layer comprising at least one Group VIII metal and the zeolite of this invention, and a second layer comprising an aluminosilicate zeolite which has different shape selectivity than the zeolite of said first layer.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and the zeolite of this invention. The zeolite may be predominantly in the hydrogen form.

Further included in this invention is a process for isomerization dewaxing a raffinate comprising contacting said raffinate in the presence of added hydrogen with a catalyst comprising at least one Group VIII metal and the zeolite of this invention. The raffinate may be bright stock, and the zeolite may be predominantly in the hydrogen form.

Also provided by the present invention is a catalytic cracking process comprising contacting a hydrocarbon feedstock in a reaction zone under catalytic cracking conditions in the absence of added hydrogen with a catalyst comprising the zeolite of this invention, preferably predominantly in the hydrogen form. Also included in this invention is such a catalytic cracking process wherein the catalyst additionally comprises a large pore crystalline cracking component.

The present invention further provides a process for oligomerizing olefins comprising contacting an olefin feed under oligomerization conditions with a catalyst comprising the zeolite of this invention.

There is further provided in accordance with this invention a process for isomerizing olefins comprising contacting an olefin feed under isomerization conditions with a catalyst comprising the zeolite of this invention.

Further provided in accordance with this invention is a process for the production of higher molecular weight hydrocarbons from lower molecular weight hydrocarbons comprising the steps of:

(a) introducing into a reaction zone a lower molecular weight hydrocarbon-containing gas and contacting said gas in said zone under $C_{2+}$ hydrocarbon synthesis conditions with a catalyst comprising the zeolite of this invention and a metal or metal compound capable of converting the lower molecular weight hydrocarbon to a higher molecular weight hydrocarbon; and (b) withdrawing from said reaction zone a higher molecular weight hydrocarbon-containing stream. Preferably, the metal or metal compound is a lanthanide or actinide metal or metal compound and the lower molecular weight hydrocarbon is methane.

This invention also provides a process for converting lower alcohols and other oxygenated hydrocarbons comprising contacting said lower alcohol or other oxygenated hydrocarbon with a catalyst comprising the zeolite of this invention under conditions to produce liquid products.

Also provided by the present invention is an improved process for the reduction of oxides of nitrogen contained in a gas stream in the presence of oxygen wherein said process comprises contacting the gas stream with a zeolite, the improvement comprising using as the zeolite the zeolite of this invention. The zeolite may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

Also provided in accordance with this invention is a process for the separation of nitrogen from a nitrogen-containing gas mixture comprising contacting the mixture with a composition comprising the zeolite of this invention. In a preferred embodiment, the gas mixture contains nitrogen and methane.

DETAILED DESCRIPTION OF THE INVENTION

SSZ-52 is prepared from a reaction mixture having the composition shown in Table A below.

TABLE A

| Reaction Mixture | |
| --- | --- |
| $YO_2/W_2O_3$ | 15–60 |
| $OH^-/YO_2$ | 0.30–1.0 |
| $Q/YO_2$ | 0.10–0.40 |
| $M_{2/n}/YO_2$ | 0.10–0.50 |
| $H_2O/YO_2$ | 15–50 | where Y, W, Q, M and n are as defined above.

In practice, SSZ-52 is prepared by a process comprising:

(a) preparing an aqueous solution containing sources of at least one oxide capable of forming a crystalline molecular sieve and Template A;

(b) maintaining the aqueous solution under conditions sufficient to form crystals of SSZ-52; and (c) recovering the crystals of SSZ-52.

Accordingly, SSZ-52 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a second tetravalent element(s) different from the first tetravalent element(s), trivalent element(s), pentavalent element(s) or mixture thereof. The first tetravalent element(s) is preferably selected from the group consisting of silicon, germanium and combinations thereof. More preferably, the first tetravalent element is silicon. The second tetravalent element (which is different from the first tetravalent element), trivalent element and pentavalent element is preferably selected from the group consisting of aluminum, gallium, iron, and combinations thereof. More preferably, the second trivalent or tetravalent element is aluminum.

Typical sources of aluminum oxide for the reaction mixture include aluminates, alumina, aluminum colloids, aluminum oxide coated on silica sol, hydrated alumina gels such as $Al(OH)_3$ and aluminum compounds such as $AlCl_3$ and $Al_2(SO_4)_3$. Typical sources of silicon oxide include silicates, silica hydrogel, silicic acid, fumed silica, colloidal silica, tetra-alkyl orthosilicates, and silica hydroxides. Gallium, germanium, and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 4,503,024 issued on Mar. 5, 1985 to Bourgogne et al. entitled "PROCESS FOR THE PREPARATION OF SYNTHETIC ZEOLITES, AND ZEOLITES OBTAINED BY SAID PROCESS", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

The organic templating agent used to prepare SSZ-52 is an N,N-diethyl-5,8-dimethyl-2-azonium bicyclo[3.2.2] nonane cation having the following structure:

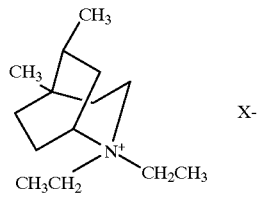

where X is an anion that is not detrimental to the formation of the SSZ-52. Representative anions include halogen, e.g., fluoride, chloride, bromide and iodide, hydroxide, acetate, sulfate, tetrafluoroborate, carboxylate, and the like. Hydroxide is the most preferred anion.

The reaction mixture is maintained at an elevated temperature until the crystals of the SSZ-52 zeolite are formed. The hydrothermal crystallization is usually conducted under autogenous pressure, at a temperature between 120° C. and 160° C. The crystallization period is typically greater than 1 day and preferably from about 3 days to about 20 days.

Preferably, the zeolite is prepared using mild stirring or agitation.

During the hydrothermal crystallization step, the SSZ-52 crystals can be allowed to nucleate spontaneously from the reaction mixture. The use of SSZ-52 crystals as seed material can be advantageous in decreasing the time necessary for complete crystallization to occur. In addition, seeding can lead to an increased purity of the product obtained by promoting the nucleation and/or formation of SSZ-52 over any undesired phases. When used as seeds, SSZ-52 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-52 zeolite crystals. The drying step can be performed at atmospheric pressure or under vacuum.

SSZ-52 as prepared has a mole ratio of an oxide selected from silicon oxide, germanium oxide and mixtures thereof to an oxide selected from aluminum oxide, gallium oxide, iron oxide, and mixtures thereof of about 6–50; and has, after calcination, the X-ray diffraction lines of Table I below. SSZ-52 further has a composition, as synthesized and in the anhydrous state, in terms of mole ratios, shown in Table B below.

TABLE B

| As-Synthesized SSZ-52 | |
|---|---|
| $YO_2/W_2O_3$ | 6–50 |
| $M_{2/n}/YO_2$ | 0.02–0.20 |
| $Q/YO_2$ | 0.02–0.08 | where Y, W, Q, M and n are as defined above.

Lower silica to alumina ratios may be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

It is believed that SSZ-52 is comprised of a new framework structure or topology which is characterized by its X-ray diffraction pattern. After calcination, the SSZ-52 zeolites have a crystalline structure whose X-ray powder diffraction pattern include the characteristic lines shown in Table I:

TABLE I

| Calcined SSZ-52 | | |
|---|---|---|
| 2 Theta[a] | D | Relative Intensity |
| 7.7 | 11.5 | W–S |
| 10.8 | 8.19 | W–S |
| 12.4 | 7.13 | W–S |
| 12.9 | 6.86 | W–VS |
| 15.1 | 5.86 | W–S |
| 16.9 | 5.24 | W–S |
| 17.85 | 4.97 | VS |
| 19.95 | 4.45 | M–VS |
| 21.35 | 4.16 | M–VS |
| 26.1 | 3.41 | M–VS |
| 30.3 | 2.95 | M–S |
| 31.25 | 2.86 | W–M |
| 34.7 | 2.58 | W–M |

[a] ±0.20

The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for calcined SSZ-52 including actual relative intensities.

TABLE IA

| Calcined SSZ-52 | | |
|---|---|---|
| 2 Theta[a] | D | Relative Intensity |
| 7.7 | 11.5 | 10–60 |
| 10.8 | 8.19 | 10–50 |
| 12.4 | 7.13 | 5–45 |
| 12.9 | 6.86 | 25–100 |
| 15.1 | 5.86 | 5–50 |
| 16.9 | 5.24 | 5–60 |
| 17.85 | 4.97 | 65–100 |
| 19.95 | 4.45 | 30–100 |
| 21.35 | 4.16 | 40–100 |
| 26.1 | 3.41 | 35–100 |
| 30.3 | 2.95 | 25–65 |
| 31.25 | 2.86 | 15–45 |
| 34.7 | 2.58 | 10–50 |

[a] ±0.20

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

Representative peaks from the X-ray diffraction pattern of calcined SSZ-52 are shown in Table I. Calcination can result in changes in the intensities of the peaks as compared to patterns of the "as-made" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-52 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. Nos. 3,140,249 issued Jul. 7, 1964 to Plank et al.; 3,140,251 issued Jul. 7, 1964 to Plank et al.; and 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-52. The zeolite can also be impregnated with the metals, or, the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank et al.; 3,140,251 issued on Jul. 7, 1964 to Plank et al.; and 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-52, the spatial arrangement of the atoms which form the basic crystal lattice of the zeolite remains essentially unchanged.

SSZ-52 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

SSZ-52 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-52 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-52 are expected to be useful include hydrocracking, dewaxing, catalytic cracking and olefin formation reactions. The catalysts are also expected to be useful in other petroleum refining and hydrocarbon conversion reactions such as isomerizing n-paraffins and naphthenes, isomerizing olefins, polymerizing and oligomerizing olefinic or acetylenic compounds such as isobutylene and butene-1, reforming, forming higher molecular weight hydrocarbons from lower molecular weight hydrocarbons (e.g., methane upgrading) and oxidation reactions. The SSZ-52 catalysts may have high selectivity, and under hydrocarbon conversion conditions can provide a high percentage of desired products relative to total products.

SSZ-52 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-52 in the hydrocarbon conversion reactions of this invention. Preferred conditions are indicated in parentheses.

| Process | Temp.,° C. | Pressure | LHSV |
|---|---|---|---|
| Hydrocracking | 175–485 | 0.5–350 bar | 0.1–30 |
| Dewaxing | 200–475 (250–450) | 15–3000 psig (200–3000) | 0.1–20 (0.2–10) |
| Cat. cracking | 127–885 | subatm.-[1] (atm.-5 atm.) | 0.5–50 |
| Oligomerization | 232–649[2] 10–232[4] (27–204)[4] | 0.1–50 atm.[2,3] — — | 0.2–50[2] 0.05–20[5] (0.1–10)[5] |
| Condensation of alcohols | 260–538 | 0.5–1000 psig | 0.5–50[5] |
| Isomerization | 93–538 (204–315) | 50–1000 psig | 1–10 (1–4) |

[1]Several hundred atmospheres
[2]Gas phase reaction
[3]Hydrocarbon partial pressure
[4]Liquid phase reaction
[5]WHSV Other reaction conditions and parameters are provided below.

Hydrocracking

Using a catalyst which comprises SSZ-52, preferably predominantly in the hydrogen form, and a hydrogenation promoter, heavy petroleum residual feedstocks, cyclic stocks and other hydrockrackate charge stocks can be hydrocracked using the process conditions and catalyst components disclosed in the aforementioned U.S. Pat. Nos. 4,910,006 and 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-52, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-52 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling above about 350° F.

A typical dewaxing process is the catalytic dewaxing of a hydrocarbon oil feedstock boiling above about 350° F. and containing straight chain and slightly branched chain hydrocarbons by contacting the hydrocarbon oil feedstock in the presence of added hydrogen gas at a hydrogen pressure of about 15–psi with a catalyst comprising SSZ-52 and at least one Group VIII metal.

The SSZ-52 hydrodewaxing catalyst may optionally contain a hydrogenation component of the type commonly employed in dewaxing catalysts. See the aforementioned U.S. Pat. Nos. 4,910,006 and 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-52 may also be utilized as a dewaxing catalyst in the form of a layered catalyst. That is, the catalyst comprises a first layer comprising zeolite SSZ-52 and at least one Group VIII metal, and a second layer comprising an aluminosilicate zeolite which has a shape selectivity different from zeolite SSZ-52. The use of layered catalysts is disclosed in U.S. Pat. No. 5,149,421, issued Sep. 22, 1992 to Miller, which is incorporated by reference herein in its entirety. The layering may also include a bed of SSZ-52 layered with a non-zeolitic component designed for either hydrocracking or hydrofinishing.

SSZ-52 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig at space velocities (LHSV) between about 0.1 and 20 and a hydrogen recycle rate of about 400 to 1500 SCF/bbl. The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-52. For example, a $C_{20+}$ lube oil may be made by isomerizing a $C_{20+}$ olefin feed over a catalyst comprising SSZ-52 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. and at a pressure of from about 15 psig to about 3000 psig in the presence of added hydrogen gas with a catalyst comprising SSZ-52 in the hydrogen form and at least one Group VIII metal.

Catalytic Cracking

Hydrocarbon cracking stocks can be catalytically cracked in the absence of hydrogen using SSZ-52, preferably predominantly in the hydrogen form.

When SSZ-52 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. Nos. 4,910,006 and 5,316,753. When a traditional cracking catalyst (TC) component is employed, the relative weight ratio of the TC to the SSZ-52 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. Nos. 4,910,006 and 5,316,753 for examples of such matrix components.

Oligomerization

It is expected that SSZ-52 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-52.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Isomerization of Olefins

SSZ-52 can be used to isomerize olefins. The feed stream is a hydrocarbon stream containing at least one $C_{4-6}$ olefin, preferably a $C_{4-6}$ normal olefin, more preferably normal butene. Normal butene as used in this specification means all forms of normal butene, e.g., 1-butene, cis-2-butene, and trans-2-butene. Typically, hydrocarbons other than normal butene or other $C_{4-6}$ normal olefins will be present in the feed stream. These other hydrocarbons may include, e.g., alkanes, other olefins, aromatics, hydrogen, and inert gases.

The feed stream typically may be the effluent from a fluid catalytic cracking unit or a methyl-tert-butyl ether unit. A fluid catalytic cracking unit effluent typically contains about 40–60 weight percent normal butenes. A methyl-tert-butyl ether unit effluent typically contains 40–100 weight percent normal butene. The feed stream preferably contains at least about 40 weight percent normal butene, more preferably at least about 65 weight percent normal butene. The terms iso-olefin and methyl branched iso-olefin may be used interchangeably in this specification.

The process is carried out under isomerization conditions. The hydrocarbon feed is contacted in a vapor phase with a catalyst comprising the SSZ-52. The process may be carried out generally at a temperature from about 625° F. to about 950° F. (329–510° C.), for butenes, preferably from about 700° F. to about 900° F. (371–482° C.), and about 350° F. to about 650° F. (177–343° C.) for pentenes and hexenes. The pressure ranges from subatmospheric to about 200 psig, preferably from about 15 psig to about 200 psig, and more preferably from about 1 psig to about 150 psig.

The liquid hourly space velocity during contacting is generally from about 0.1 to about 50 $hr^{-1}$, based on the hydrocarbon feed, preferably from about 0.1 to about 20 $hr^{-1}$, more preferably from about 0.2 to about 10 $hr^{-1}$, most preferably from about 1 to about 5 $hr^{-1}$. A hydrogen/hydrocarbon molar ratio is maintained from about 0 to about 30 or higher. The hydrogen can be added directly to the feed stream or directly to the isomerization zone. The reaction is preferably substantially free of water, typically less than about two weight percent based on the feed. The process can be carried out in a packed bed reactor, a fixed bed, fluidized bed reactor, or a moving bed reactor. The bed of the catalyst can move upward or downward. The mole percent conversion of, e.g., normal butene to iso-butene is at least 10, preferably at least 25, and more preferably at least 35.

Methane Upgrading

Higher molecular weight hydrocarbons can be formed from lower molecular weight hydrocarbons by contacting the lower molecular weight hydrocarbon with a catalyst comprising SSZ-52 and a metal or metal compound capable of converting the lower molecular weight hydrocarbon to a higher molecular weight hydrocarbon. Examples of such reactions include the conversion of methane to $C_{2+}$ hydrocarbons such as ethylene or benzene or both. Examples of useful metals and metal compounds include lanthanide and or actinide metals or metal compounds.

These reactions, the metals or metal compounds employed and the conditions under which they can be run are disclosed in U.S. Pat. No. 4,734,537, issued Mar. 29, 1988 to Devries et al.; U.S. Pat. No. 4,939,311, issued Jul. 3, 1990 to Washecheck et al.; U.S. Pat. No. 4,962,261, issued Oct. 9, 1990 to Abrevaya et al.; U.S. Pat. No. 5,095,161, issued Mar. 10, 1992 to Abrevaya et al.; U.S. Pat. No. 5,105,044, issued Apr. 14, 1992 to Han et al.; U.S. Pat. No. 5,105,046, issued Apr. 14, 1992 to Washecheck; U.S. Pat. No. 5,238,898, issued Aug. 24, 1993 to Han et al.; U.S. Pat. No. 5,321,185, issued Jun. 14, 1994 to van der Vaart; and U.S. Pat. No. 5,336,825, issued Aug. 9, 1994 to Choudhary et al., each of which is incorporated herein by reference in its entirety.

Condensation of Alcohols

SSZ-52 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Other Uses for SSZ-52

SSZ-52 can also be used as an adsorbent with high selectivities based on molecular sieve behavior and also based upon preferential hydrocarbon packing within the pores.

SSZ-52 may also be used for the catalytic reduction of the oxides of nitrogen in a gas stream. Typically, the gas stream also contains oxygen, often a stoichiometric excess thereof. Also, the SSZ-52 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a zeolite is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

SSZ-52 may also be used in the separation of gases, such as the separation of nitrogen from a nitrogen-containing gas mixture. One example of such separation is the separation of nitrogen from methane (e.g., the separation of nitrogen from natural gas).

EXAMPLES

The following examples demonstrate but do not limit the present invention.

Example 1

Synthesis of N,N-diethyl-5,8-dimethyl-2-azonium bicyclo[3.2.2]nonane cation (Template A)

A three-neck, 5-liter flask is set up with additional funnel with equalization arm. A septum is place over the funnel. Nitrogen is passed through the system. First an in-situ reagent is developed by placing 104.55 grams of diisopropylamine in 1859 ml of tetrahydrofuran (THF) and then slowly adding 401.7 ml of n-butyl lithium (2.5 M in hexane) while keeping the temperature near −70° C. The n-butyl lithium is charged to the addition funnel by use of a cannula. The addition into THF takes about 1.25 hours after which the resulting mixture is stirred for another hour. 104.53 grams of 3-methyl-2-cyclohexene-1 one in 1117 ml THF is added dropwise over a 0.75 hour period. Lastly, 161.73 grams of methyl acrylate is added over a period of 0.25 hour. Gradually, the reaction is allowed to warm to room temperature and its progress is followed by TLC. The reaction appears to go overnight.

Recovery of the product is begun by adding 1N HCl until the solution becomes acidic. The reaction product is transferred to separatory funnel and the aqueous phase is recovered to subsequently treat with methylene chloride (2×250 ml). The combined organic phase is dried over sodium sulfate and then strip solvent. The residue is taken up in ether to free it from a little gummy material. The ether is removed and the resulting oil is distilled; a Vigreaux column (30 cm) is set up and run at 2–4 mm Hg. The bulk of the product comes over between 123–137° C.

The resulting product is reduced using lithium aluminum hydride. The reduction produces a diol, 1-methyl-2-methanol-7-hydroxy bicyclo[2.2.2]octane. The side methanol group is tosylated by reaction of tosyl chloride (96.92 grams) with the diol (85.68 grams) in anhydrous pyridine (500 ml). The tosyl chloride is added to the other two components, under nitrogen, using a powder addition funnel while cooling the reaction to −5° C. The addition is carried out over 0.75 hour and the reaction mixture is warmed to room temperature and the reaction is allowed to run overnight. 500 ml of methylene chloride is added, the resulting mixture transferred to a separatory funnel, and washed with water (2×250 ml). The resulting product is dried over sodium sulfate, filtered, and stripped to yield 150 grams of oil.

The product is purified by column chromatography. A kilogram of silica gel (230–400 mesh) is slurried in hexane, and the oil is loaded on top in 50 ml methylene chloride. The elution is carried out using 25/75 ethyl acetate (ETOAC); hexane and fractions are monitored by TLC. Eighty-three grams of product is collected. The tosylate is then reduced using LAH (as above) to yield 1,2-dimethyl-7-hydroxy bicyclo[2.2.2]octane. Next, the alcohol is reoxidized to the ketone. 37.84 grams of the alcohol is reacted in a three-neck, 2-liter flask as follows: 34.60 grams of oxalyl chloride and 604 ml of methylene chloride are loaded in and blanketed under nitrogen. With an addition funnel with side arm, 46 grams of anhydrous dimethylsulfoxide (DMSO) in 122.7 ml of methylene chloride is added. The bath is cooled to −60° C. using a dry ice/acetone bath, and the addition takes 0.5 hour. The alcohol, in 53.4 ml methylene chloride, is added at this temperature over 0.5 hour followed by stirring for another 0.5 hour. 126.65 Grams of triethylamine is then placed in the addition funnel and addition begun and continued over 0.25 hour. All of the additions produce exothermic response, so cooling is continued. The reaction mixture is slowly warmed to room temperature and the reaction continued to run overnight.

Work-up of the reaction product begins with addition of 500 ml water. The separated aqueous phase is then extracted with methylene chloride (2×250 ml). The combined organic phases are then dried over magnesium sulfate and stripped. The resulting oil is triturated with ether to separate a small amount of insoluble material. Stripping off ether yields 37 grams of product.

Thirty-seven grams of ketone and 240 ml of 96% formic acid are placed into a 1 liter round bottom flask connected to an addition funnel. These components are stirred using a magnetic stir bar. 125 Ml of formic acid with 43 grams of hydroxylamine-O-sulfonic acid dissolved and suspended in it, are added to the funnel. The addition is carried out over a 20 minute period with stirring. The solution darkens. The addition funnel is replaced with a reflux condenser, and the reaction is refluxed for 15–20 hours with samples taken to follow by TLC.

The mixture is carefully poured into 2 kg of ice. After cooling in the ice, the mixture is slowly brought to pH=12 with the addition of 50% NaOH. Three extractions are carried out using 500 cc units of methylene chloride. These extracts are dried over sodium sulfate. After drying, the solvent is stripped off leaving a black oil of about 45 grams.

This oil is dissolved in a minimum of chloroform and loaded onto a column (750 grams of 230–400 mesh silica gel, already slurried in chloroform). The elution progresses using chloroform with 2 vol. % methanol. The elution fractions are followed by TLC (fractions 7–21 give the same product). The similar fractions are combined and removing the eluting solvent yields about 30 grams of lactam.

25 Grams of this lactam is used in the reduction step. Using a 2 liter 3-neck round bottom flask, nitrogen gas is run into the system and vented up through the reflux condenser and into a bubbler. The system has an addition funnel. 460 Ml of anhydrous ether are added into the flask. Carefully, 18 grams of lithium aluminum hydride are also admitted into the flask. There is some gas evolution. The lactam is dissolved in 230 ml of methylene chloride (also anhydrous). After cooling the flask down in an acetone/dry ice bath, the lactam is added dropwise. The reaction is exothermic so periodically more ice needs to be added as temperature rises. The reduction can be followed by change in TLC data (monitored by iodine and eluted on silica with 98/2 chloroform/methanol). The reaction is allowed to come to room temperature overnight.

18 Grams of water are slowly added with the expected exothermic evolution of gas occurring. The ether is removed and its volume replaced with dichloromethane. 18 Grams of 15% NaOH solution and then 55 grams of water are added. The solids which form are filtered off, washed with additional dichloromethane, and combined with the organic fractions and dry over sodium sulfate (Caution: Do not let the NaOH solution sit in contact with dichloromethane overnight.). The solvent is stripped off to recover about 15 grams of oil/solid mix. This is the crude amine.

10 grams of this amine is quaternized as follows: In a 250 ml flask equipped with stir bar and reflux condenser add the amine, 10 grams of KHCO3, 65 ml of methanol and lastly, 30 grams of ethyl iodide. The mixture is brought to reflux and maintained in that state for 48 hours. Upon cooling, the solvent is removed. The solids are treated with chloroform. In turn the chloroform-soluble fractions are stripped to yield another solid which is recrystallized from a minimum of hot acetone and methanol. Recrystallization in the cold yields 3 separate crops of product, totaling 11 grams of the salt. The melting points for these crops are all in the range of 252–256° C.

The salt is converted to the hydroxide form by ion-exchange over a BioRad AG1-X8 resin.

Example 2

Synthesis of SSZ-52

3.36 Grams of Template A (0.596 M) is placed in the Teflon cup of a 23 ml Parr reactor. Next, 0.20 gram of 1.0 N NaOH and 2.26 grams of water are added. 2.5 Grams of Banco N silicate is added (NaOH/SiO$_2$=0.59 and SiO$_2$ is about 28 weight percent). 0.25 Grams of sodium Y zeolite is added as a source of aluminum. The reaction vessel is closed and heated at 135° C. with 43 RPM tumbling. The reaction is run for seven days. Upon cooling the reaction mixture to room temperature, the pH is 12.36 indicating that crystallization has occurred. A crystalline product is recovered and determined by X-ray diffraction to be SSZ-52. The XRD data appears in Table II below.

TABLE II

| 2 Theta | D | I/I$_0$ × 100 |
|---|---|---|
| 7.7 | 11.47 | 46 |
| 8.46 | 10.44 | 8 |
| 10.75 | 8.22 | 20 |
| 12.41 | 7.13 | 28 |
| 12.94 | 6.84 | 37 |
| 15.11 | 5.86 | 4 |
| 15.49 | 5.72 | 16 |
| 16.86 | 5.25 | 46 |
| 17.78 | 4.99 | 94 |
| 19.97 | 4.44 | 78 |
| 21.33 | 4.16 | 100 |
| 22.14 | 4.01 | 17 |
| 22.53 | 3.94 | 22 |
| 26.09 | 3.41 | 77 |
| 26.84 | 3.32 | 17 |
| 27.2 | 3.28 | 12 |
| 28.26 | 3.16 | 8 |
| 28.97 | 3.08 | 14 |
| 30.29 | 2.95 | 47 |
| 31.24 | 2.86 | 34 |
| 31.81 | 2.81 | 12 |
| 32.73 | 2.73 | 19 |
| 34.72 | 2.58 | 37 |
| 38.88 | 2.31 | 5 |
| 39.44 | 2.28 | 8 |

Example 3

Synthesis of SSZ-52

A reaction is carried out as described in Example 2. A new solution of Template A is used with a 0.527 M value as the hydroxide salt. 3.80 Grams of Template A is used and the other reagents are the same as in Example 2. Eleven days are required to crystallize a product that is identified as SSZ-52.

Example 4

Calcination of SSZ-52

The material from Example 2 is calcined in the following manner. A thin bed of material is heated in a muffle furnace from room temperature to 120° C. at a rate of 1° C. per minute and held at 120° C. for three hours. The temperature is then ramped up to 540° C. at the same rate and held at this temperature for 5 hours. A 50/50 mixture of air and nitrogen is passed over the zeolite at a rate of 20 standard cubic feet per minute during heating. The X-ray diffraction data for the product is provided in Table III below.

TABLE III

| 2 Theta | D | I/I$_0$ × 100 |
|---|---|---|
| 7.74 | 11.41 | 21 |
| 8.43 | 10.48 | 6 |
| 10.80 | 8.19 | 37 |

TABLE III-continued

| 2 Theta | D | I/I₀ × 100 |
|---|---|---|
| 12.47 | 7.09 | 15 |
| 12.92 | 6.85 | 100 |
| 15.09 | 5.87 | 17 |
| 15.41 | 5.75 | 7 |
| 15.67 | 5.65 | 2 |
| 16.88 | 5.25 | 18 |
| 17.91 | 4.95 | 77 |
| 19.95 | 4.45 | 45 |
| 20.17 | 4.40 | 25 |
| 21.33 | 4.16 | 67 |
| 22.21 | 4.00 | 29 |
| 26.05 | 3.42 | 47 |
| 27.06 | 3.29 | 13 |
| 28.29 | 3.15 | 6 |
| 29.08 | 3.07 | 9 |
| 29.41 | 3.04 | 3 |
| 30.26 | 2.95 | 32 |
| 31.22 | 2.86 | 29 |
| 31.85 | 2.81 | 15 |
| 32.82 | 2.73 | 11 |
| 33.22 | 2.70 | 3 |
| 34.69 | 2.58 | 21 |
| 38.86 | 2.32 | 3 |
| 39.46 | 2.28 | 4 |

Example 5

NH₄ Exchange of SSZ-52

Ion exchange of calcined SSZ-52 material (prepared in Example 4) is performed using $NH_4NO_3$ to convert the zeolite from its $Na^+$ form to the $NH_4^+$ form, and, ultimately, the $H^+$ form. The same mass of $NH_4NO_3$ as zeolite is slurried in water at a weight ratio of 20:1 water to zeolite. The exchange solution is heated at 90° C. for 2 hours and then filtered. This procedure can be repeated up to three times. Following the final exchange, the zeolite is washed several times with water and dried. This $NH_4^+$ form of SSZ-52 can then be converted to the $H^+$ form by calcination (as described in Example 4) to 540° C.

Example 6

Micropore Volume of SSZ-52

The argon adsorption capacity of the SSZ-52 is measured using an Omnisorp 100CX instrument. Fifty mg samples of SSZ52 are used. After evacuation of the sample in the cell at room temperature, the temperature is raised to 300° C. while keeping the cell under vacuum. These conditions are held for two hours. The cell and sample are then cooled to 87 Kelvin in a reservoir of liquid argon. In a static micropore filling measurement, doses of argon from a calibrated volume are admitted to the cell at successively higher pressures. The amounts that adsorb from each dose are calculated from the pressure changes. Micropore filling is detected as a step increase in a plot of amount adsorbed versus pressure. The position of the step defines a $P/P_0$ for micropore filling and its size indicates the adsorption capacity of the micropores.

Two peaks are found for calcined SSZ-52 (from Example 4) using argon and static uptake measurements. Both peaks are in the range of 20–30 microbars. The combined micropore volume is quite high and equals 0.34 cc/gm of micropore volume.

Example 7

Use of SSZ-52 To Convert Methanol

130 Milligrams of SSZ-52, as prepared in Example 2, 4 and 5 is pressed in a Carver press to 3 KPSI. The material is slightly chipped to maintain a +40 mesh fraction. The material is calcined in air to 1100° F. (593° C.) and then packed into a ⅜ inch stainless steel reactor. The catalyst is supported on glass wool and the bed is preceded by a zone of acid-washed alundum. The reactor is loaded into a Lindberg furnace and the catalyst is equilibrated at 400° C. in a stream of nitrogen (20 cc/min.). The feed is then introduced by syringe pump (1.31 cc/hr) and is 22.1 wt. % methanol in water.

A first sample is taken at 10 minutes on stream, via a Valco sampling valve. The conversion of methanol is 95% with almost all the products consisting of $C_2$–$C_5$ hydrocarbons. No aromatics are detected. The catalyst loses activity with time-on-stream, dropping to about 5% conversion over a 3 hour period. The test reaction demonstrates that SSZ-52 can be used for the conversion of methanol to olefins (MTO). The data is also consistent with a view that SSZ-52 could be an 8-ring, small pore zeolite.

What is claimed is:

1. A zeolite having a mole ratio of about 6–50 of an oxide selected from the group consisting of silicon oxide, germanium oxide and mixtures thereof to an oxide selected from aluminum oxide, gallium oxide, iron oxide and mixtures thereof, and having, after calcination, the X-ray diffraction lines of Table I.

2. A zeolite according to claim 1 wherein the oxides comprise silicon oxide and aluminum oxide.

3. A zeolite according to claim 1 wherein said zeolite is predominantly in the hydrogen form.

4. A zeolite according to claim 1 wherein said zeolite is substantially free of acidity.

5. A zeolite having a composition, as synthesized and in the anhydrous state, in terms of mole ratios as follows:

| | |
|---|---|
| $YO_2/W_2O_3$ | 6–50 |
| $M_{2/n}/YO_2$ | 0.03–0.25 |
| $Q/YO_2$ | 0.02–0.08 | wherein Y is silicon, germanium or a mixture thereof; W is aluminum, gallium, iron or mixtures thereof; M is an alkali metal cation, alkaline earth metal cation or mixtures thereof; n is the valence of M; and Q is a quaternary ammonium cation having the structure

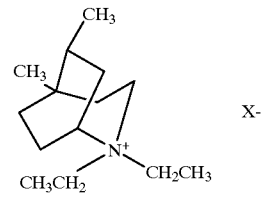

where X— is an anion which is not detrimental to the formation of the zeolite.

6. A zeolite according to claim 5 wherein W is aluminum and Y is silicon.

7. A method of preparing a crystalline material comprising an oxide selected from silicon oxide, germanium oxide and mixtures thereof to an oxide selected from aluminum oxide, gallium oxide, iron oxide, and mixtures thereof, said method comprising contacting under crystallization conditions sources of said oxides and a templating agent comprising a quaternary ammonium cation having the structure

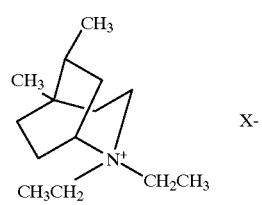
where X— is an anion which is not detrimental to the formation of the crystalline material.
8. The method according to claim 7 wherein the oxides are silicon oxide and aluminum oxide.
9. The method of claim 7 wherein the crystalline material has, after calcination, the X-ray diffraction lines of Table I.
* * * * *